United States Patent [19]

Narayanan et al.

[11] Patent Number: 4,892,096

[45] Date of Patent: Jan. 9, 1990

[54] BREAST MARKING DEVICE

[75] Inventors: Krishna Narayanan; Marc D. Liang, both of Pittsburgh, Pa.

[73] Assignee: Montefiore Hospital Association of Western Pennsylvania, Pittsburgh, Pa.

[21] Appl. No.: 270,420

[22] Filed: Nov. 9, 1988

Related U.S. Application Data

[63] Continuation of Ser. No. 57,117, Jun. 3, 1987, abandoned.

[51] Int. Cl.⁴ ............................................ A61B 17/00
[52] U.S. Cl. ..................................................... 606/1
[58] Field of Search ........... 128/305, 316, 310, 303 R; 33/297, 670, 671; 30/316

[56] References Cited

U.S. PATENT DOCUMENTS

| | | | |
|---|---|---|---|
| 3,119,185 | 1/1964 | Gray | 33/297 |
| 3,546,778 | 12/1970 | Lepkowski | 33/297 |
| 4,336,805 | 6/1982 | Smirmaul | 128/310 |
| 4,705,035 | 11/1987 | Givens | 128/316 X |

*Primary Examiner*—Michael H. Thaler
*Attorney, Agent, or Firm*—Harry B. Keck

[57] ABSTRACT

A marking device provides a circular mark on the skin of the breast of a patient concentric with the areola of the patient's breast. The device is a cylindrical tubular member having an open circular end which is the marking element and having a pair of cross markings at the other end on an optically transparent wall to permit optical centering of the device with respect to the breast areola prior to skin marking. A preferred embodiment includes a pair of markers in a common cylindrical tubular member having one circular diameter at one end and a different circular diameter at the other end.

6 Claims, 1 Drawing Sheet

BREAST MARKING DEVICE

CROSS REFERENCE TO RELATED APPLICATIONS

This application is a continuation of application Ser. No. 057,117 filed June 3, 1987, abandoned.

BACKGROUND OF THE INVENTION

1. Field of the Invention

This invention relates to a method and apparatus for providing a visible mark on the breast of as surgical patient which is concentric with the areola of the patient's breast.

2. Description of the Prior Art

In breast reconstruction surgical procedures, it is commonplace to remove skin and tissue in the region outside the breast areola, which, desirably, is maintained in its normal, central location. The accepted procedure is to stamp an inked circle from the circular open end of a cylindrical inked marking device. The application of ink to the patient's skin may be objectionable, but more importantly, the existing marker devices frequently provide the circular marking eccentrically of the breast areola.

The normal procedure for breast reduction surgery is to provide a circular incision which is concentric to the breast areola and to remove and reconstruct tissue peripherally outside the circular incision. This procedure results in an esthetically satisfactory appearance of the reconstructed breast. In cases where the initial circular incision is eccentric to the breast areola, the reconstructed breasts may be undesirably non-symmetrical.

Accordingly, there is a need for a marking device for use in reconstructive breast surgery which can provide a invisible, non-permanent circular mark which is concentric to the breast areola.

STATEMENT OF THE INVENTION

According to the present invention, a cylindrical marking device is provided with a circular opening at one end and a closed wall at the other end. The closed wall is transparent, at least at its central region, and is provided with visible cross-markings (sometimes called cross-hairs) which intersect on the longitudinal axis of the cylinder. The open circular surface has a tapered rim presenting a thin edge.

The device is applied to a patient's breast, surmounting the breast areola and is adjusted until the crossmarkings of the flat wall are aligned with the center of the breast areola. The device then is pressed against the patient's breast and may be rotated about the longitudinal axis of the cylinder whereby the thin circular edge creates a visible, reddened circular mark which is concentric to the patient's breast areola.

The marking device thereafter may be discarded or may be sterilized for reuse. In a preferred embodiment the breast marking device is fabricated entirely from a clear plastic substance such as polycarbonate, polystyrene, or other inexpensive, easily molded transparent materials.

In a preferred embodiment, the device has two cylindrical portions having a common longitudinal axis and a common flat wall. One of the two cylindrical portions has a greater diameter than the other. This permits the selection of an appropriate size circle mark according to the patient's anatomy and the particular procedure for which the circular mark is applied.

The present device does not leave any permanent marks on the patient's skin. The skin reddening remains clear and distinct for a sufficient time to permit the surgeon to make the initial circular incision which is critical to successful breast reconstruction surgery. The circular marking normally disappears before the surgical procedures are completed.

In a still further embodiment, the intersecting lines on the flat wall portion may be enclosed within one or more circular marks to facilitate the optical centering of the device over the patient's areola before the circle is established.

DESCRIPTION OF THE PREFERRED EMBODIMENTS

Figure 1:
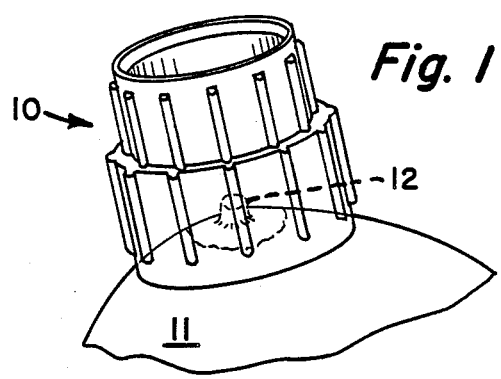
FIG. 1 is a perspective illustration of the breast marking device in its operative position.
Figure 2:
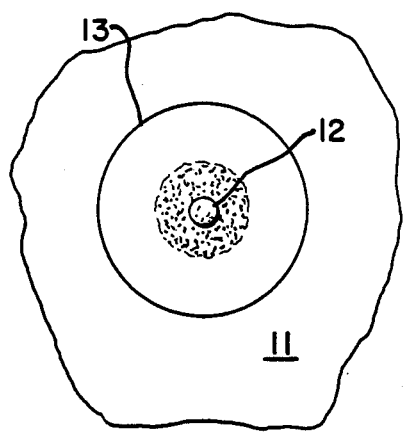
FIG. 2 is a plan view of the aerola of a patient's breast with the skin marking created by the present invention.

The breast marking device 10 of this invention is illustrated in FIG. 1 positioned on the breast 11 of a surgical patient in concentric alignment with the breast areola 12. The marking device 10 is pressed against the skin of the breast 11 and twisted to create a circular surface mark 13 on the skin of the breast 11 as shown in FIG. 2.

The preferred embodiment of the marking device 10 includes a first cylindrical tubular member 14 and a second cylindrical tubular member 15. The tubular members are joined in a central transition region 16 by a wall member 17 which is normal to the common longitudinal central axis 18 of the two concentric cylindrical tubular members 14, 15. A shoulder 19 is illustrated as an annular surface extending outwardly from the first cylindrical tubular member 14. The shoulder 19 could be a tapered surface.

The wall member 17 preferably is transparent, at least in its central portion. The transparent central portion of the wall 17 is provided with two cross marking lines 20, 21 which intersect at right angles on the longitudinal central axis 18. If desired, one or more concentric circles 22, 23 are provided on the wall 17. The marking device 10 can be positioned as shown in FIG. 1 by having the user bring the cross marking lines 20, 21 into registry with the center of the patient's breast areola 12. The circular marks 22, 23 also facilitate in the optical positioning of the marking device.

The open circular edges 24, 25 of each of the cylindrical tubular members 14, 15 respectively, are tapered to a narrow edge indicated at 26, 27 respectively, to provide a sharp skin marking element. The skin-engaging surface of the narrow edge may be about 0.5 millimeters wide.

The outer surfaces of the cylindrical tubular members 14, 15 may be provided with external beads 28 (on the cylindrical tubular member 14), 29 (on the second cylindrical tubular member 15) to provide structural rigidity to the device and to facilitate handling the device in use.

Figure 5:
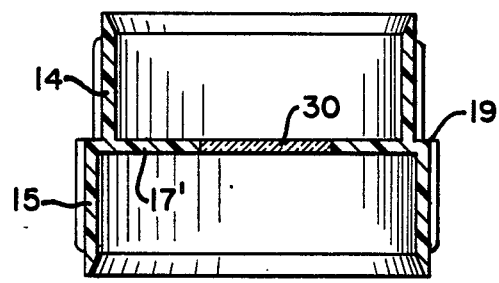
FIG. 5 is a fragmentary illustration of a wall member of an alternative embodiment of the present invention.

While the marking device 10 preferably is fabricated from transparent plastic materials, it may be fabricated from opaque materials as illustrated in FIG. 5 wherein a wall member 17' is provided with a central transparent portion 29 which contains the cross marking 20, 21 and may contain one or more concentric circles 22, 23. (Note the markings 20, 21 and circles 22, 23 are not visible in FIG. 5).

In a preferred embodiment, the first cylindrical tubular member 14 has a marking diameter of about 38 millimeters; the second cylindrical tubular member 15 has a marking diameter of about 42 millimeters. The two different sizes permit the user to select the appropriate diameter circle for the requirements of the patient and for the requirements of the surgical procedure. The height of the marking device 10 is about 30 millimeters.

Figure 3:
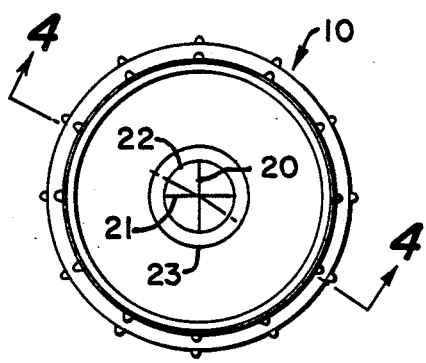
FIG. 3 is a plan view of a preferred embodiment of the present invention.
Figure 4:
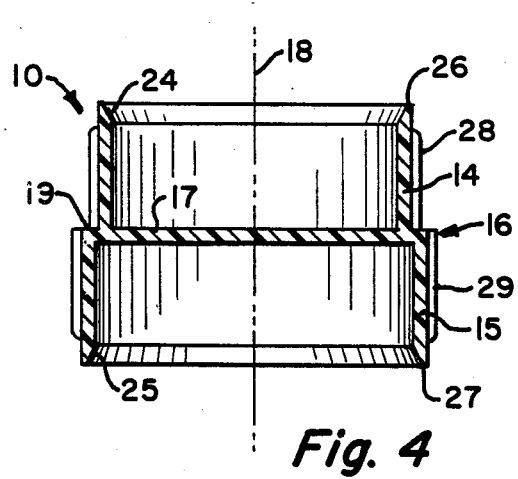
FIG. 4 is a cross-section view taken along the line EB of FIG. 3.
Figure 6:
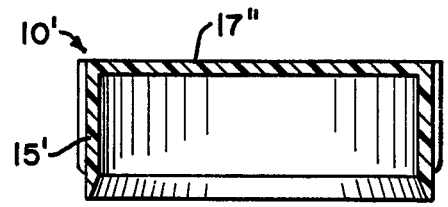
FIG. 6 is a perspective illustration of an alternative embodiment of the marking device.

The marking device 10 may be made in a single cup as shown in FIG. 6 which includes a cylindrical tubular member 15' and a flat wall member 17" corresponding to the bottom portion of the device illustrated in FIGS. 3 and 4.

We claim:

1. A device for creating a circular skin-discoloration mark on the surface of a human breast having an areola, said device comprising an optically transparent tubular member open at each end and having a generally circular cross section, one of the open ends of said tubular member having a greater diameter than the other open end; each of the two open ends comprising a circular marking edge; a wall member between the open ends extending across said tubular member substantially normal to the longitudinal central axis of said tubular member and being optically transparent; sighting means on said wall member comprising a pair of cross-markings intersecting at the central longitudinal axis of the said tubular member.

2. The marking device of claim 1 wherein the said tubular member is cylindrical adjacent each of its ends and is provided with a central transition region joining the large diameter cylindrical portion with the small diameter cylindrical portion.

3. The marking device of claim 1 having outwardly extending reinforcing beads on the outer surface of said tubular member.

4. The marking device of claim 1 including at least one circle mark on the said wall member concentric with the intersection of the two said cross-markings.

5. A marking device for creating a circular skin-discoloration mark on the surface of a human breast having an areola, said device comprising an optically transparent tubular member having a generally circular cross-section, and being open at one end and having a generally circular cross section, closed by an optically transparent flat wall member at the other end; the open end of said tubular member comprising a circular marking edge; sighting means on said wall member and comprising a pair of cross-markings intersecting at the central longitudinal axis of the said tubular member.

6. The marking device of claim 5 having outwardly extending reinforcing beads on the outer surface of said tubular member.

* * * * *